United States Patent [19]
Chan et al.

[11] Patent Number: 6,042,751
[45] Date of Patent: Mar. 28, 2000

[54] THICK FILM CONDUCTOR COMPOSITION FOR USE IN BIOSENSORS

[75] Inventors: Man-Sheung Chan; Donald W. Kuty, both of Chapel Hill, N.C.

[73] Assignee: E. I. du Pont de Nemours and Company, Wilmington, Del.

[21] Appl. No.: 09/156,309

[22] Filed: Sep. 17, 1998

[51] Int. Cl.[7] .............................. H01B 1/22; H01B 1/24; C25B 11/08; C25B 11/12
[52] U.S. Cl. ........................ 252/511; 252/514; 430/212; 430/218; 204/292; 204/294
[58] Field of Search .................................. 252/511, 514; 430/209, 212, 218; 204/280, 292, 294

[56] References Cited

U.S. PATENT DOCUMENTS

| | | | |
|---|---|---|---|
| 3,539,455 | 11/1970 | Clark et al. | 27/46 |
| 4,081,423 | 3/1978 | Hardenfelt | 260/40 R |
| 4,970,145 | 11/1990 | Bennetto et al. | 435/14 |
| 5,378,628 | 1/1995 | Gratzel et al. | 435/288 |
| 5,653,918 | 8/1997 | Towlson | 252/514 |

FOREIGN PATENT DOCUMENTS

| | | |
|---|---|---|
| 0 757 246 A2 | 2/1997 | European Pat. Off. . |
| WO98/20331 | 5/1998 | WIPO . |

OTHER PUBLICATIONS

Frew et al., *Analytical Chemistry,* 59, No. 15, 933–944, 1987.
Henning et al., *Chemical Analysis,* 148, 3–46, 1998.
Guilbault et al., *Anal. Chim. Acta.,* 64, 439–455,1973.
Cass et al., *Analytical Chemistry,* 56, No. 4, 667–671, 1984.
M. Pishko, *TRIP,* 3, 342–347, 1995.
Ikeda et al., *Agric. Biol. Chem.,* 51, 747–754, 1987.
Mizutani et al., *Cygnus, Inc.,* 60, 1141–1142,1992.
Wring et al., *Analyst,* 117, 1215–1229, 1992.
Tamada et al., *Nature Medicine,* 1, 1198–1200, 1995.
Tierney et al., Preprint from RTP Oak Ridge Conference Jun. 1998.
Lo Garton, *Analytica Chimica Acta.,* 178, 247–253, 1985.
Linke et al., *Biosensors & Bioelectronics,* 9, 151–158, 1994.

*Primary Examiner*—Mark Kopec

[57] ABSTRACT

The invention is directed to polymer thick film conductor compositions comprising conductive metal particles selected from the group consisting of finely divided powders of platinum group metals and mixtures thereof; modified graphite; and a thermoplastic polymer and optionally, graphite and/or a metallized graphite in combination with a surfactant may replace the modified graphite.

7 Claims, No Drawings

THICK FILM CONDUCTOR COMPOSITION FOR USE IN BIOSENSORS

FIELD OF INVENTION

This invention relates to a polymer thick film (PTF) composition containing a metal catalyst and graphite, which can be used to print sensing/working electrodes for electrochemical biosensors based on hydrogen peroxide detection. Electrochemical biosensors which are combinations of an electrochemical sensor and a biomolecule recognition element are useful in the analyses of biological analytes such as glucose, cholesterol, creatinine, alcohol, uric acid and lactate in body fluid, and are therefore useful in the field of medical devices and analytical instruments for medical diagnostics.

BACKGROUND OF THE INVENTION

The majority of amperometric electrochemical biosensors fall within two categories (1) metal-catalyzed electrochemical biosensors or (2) electron-transfer mediator modified electrochemical biosensors. For example, a metal-catalyzed glucose sensor detects the hydrogen peroxide by-product which is produced in a one-to-one ratio from glucose through an enzyme-catalyzed air oxidation process, such as:

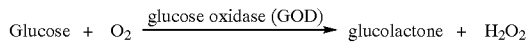

$$\text{Glucose} + O_2 \xrightarrow{\text{glucose oxidase (GOD)}} \text{glucolactone} + H_2O_2$$

U.S. Pat. No. 3,539,455 (1970) by Clark discloses a platinum based glucose sensor useful for self-monitoring of glucose by diabetics. Guilbault and Lubrano (1973) reported amperometric biosensors having an immobilized-enzyme platinum electrodes suitable for glucose sensor applications. Mizutani et al. (1992) reported a platinum/carbon paste (CP) composition with a 1/9 Pt/C ratio suitable for making glucose sensors. U.S. Pat. No. 4,970,145 (1990) to Bennetto et al. discloses a biosensor with a porous enzyme electrode comprising platinized carbon paper having a fluoropolymer binder. These platinum/C based biosensors have sensitivity for detection of glucose only at concentrations of millimolar (mM) glucose with an electric current response of <20 uA/cm$^2$.mM glucose. Furthermore, the use of a metal or metal/carbon with a high metal content as the working electrode leads to high material costs and has a drawback of loosing hydrogen peroxide due to the metal-catalyzed decomposition of hydrogen peroxide.

An electron-transfer mediator modified electrochemical biosensor relies on a fast electron-transfer mediator, which is typically an outer-sphere metal complex or organic compound, to assist the shuttling of electrons from reduced enzyme molecules to the working electrode. The reduced enzyme results from an enzyme molecule receiving two electrons from a glucose molecule, such as:

$$\text{Glucose} + (\text{GOD})_{oxidized} \rightarrow \text{Glucolactone} + (\text{GOD})_{reduced}$$

Electrochemical biosensors having carbon based working electrodes modified with electron-transfer mediators have been reviewed by Wring and Hart (1992). Biosensors having working electrodes modified with redox polymers have been reviewed by Pishko (1995). These mediator modified biosensors are capable of measuring glucose at mM concentration with an electric current response of <20 uA/cm$^2$.mM glucose. There remains a need for materials suitable for fabrication of enzyme electrodes with high catalytic activity/ current response and low background current noise to expand the capability of biosensors for monitoring biological analytes at the micro-molar (uM) level and to assure a high confidence of detecting low level of analystes in body fluids. One example was given by Tamada, Bohannon and Potts (1995) who reported the iontophoretic extraction of body fluid. The body fluid can then be analyzed in situ for a glucose levels and thus provide a method for non-invasive monitoring of glucose. The glucose concentration in the extracted body fluid is typically in the micro-molar level which produced electric current in the nano-ampere (nA) level, and thus requires a biosensor with low detection limit of glucose determination. A key limiting factor which affects the glucose detection limit is electrochemical signal noise or background current, which may be from electrochemically active impurities or temperature fluctuation etc. It is desirable that a biosensor has low background current which also does not greatly vary with temperature fluctuation.

Furthermore, it is desirable that catalyst materials for the working electrode be low cost and suitable for low cost fabrication of disposable biosensors by conventional printing processes. It is the object of the invention to overcome the deficiencies of current carbon-based materials for working electrodes.

SUMMARY OF INVENTION

The invention is directed to a polymer thick film conductor composition comprising, based on solids: (a) 0.1–5% wt. conductive metal particles selected from the group consisting of finely divided powders of platinum group metals and mixtures thereof; (b) 62–85% wt. of modified graphite; and (c) 14–35% wt. of a thermoplastic polymer.

The invention is further directed to a conductor composition for use in electrochemical sensor applications, comprising, based on solids: (a) 0.1–5% wt. conductive metal particles selected from the group consisting of finely divided powders of platinum group metals and mixtures; (b) 62–85% wt. of graphite; (c) 14–35% wt. of a thermoplastic polymer; and (d) 0.01–3% wt. surfactant.

The invention is still further directed to a conductor composition for use in electrochemical sensor applications comprising, based on solids: (a) metallized particles comprising platinum group metal particles and mixtures thereof deposited on graphite support particles; with the provisos that (1) the platinum group metal particles and mixtures thereof are in the range of 0.1–5% wt. and (2) the graphite support particles are in the range of 62–85% wt.; (b) 14–35% wt. thermoplastic polymer; and (c) 0.01–3% wt. surfactant.

DETAIL DESCRIPTION OF THE INVENTION

The PTF compositions covered in the present invention are intended for use in printing sensing or working electrodes in electrochemical biosensor applications, and more specifically, amperometric glucose sensors. The PTF composition offers glucose sensors with enzyme electrodes extremely high sensitivity for analysis of glucose at micromolar levels, for example, a method for non-invasive monitoring of analytes transdermally extracted from the body.

The PTF conductive composition is designed to have the following characteristics when used as a working electrode:

(a) Printed PTF working electrodes have high electrocatalytic activity toward a target chemical or biomolecule, and therefore are able to provide strong electrical signal even at extremely low concentrations of the target chemical. Furthermore, the PTF working electrode should not introduce background current signal noise which would limit the ability of a biosensor to detect low concentrations of a target chemical.

(b) The PTF conductive composition is designed to have stable and consistent electrocatalytic activity enabling the biosensor to handle multiple analyses for continual glucose monitoring.

c) The PTF composition is intended for use in manufacturing of disposable biosensors and it is designed to be low cost.

d) The PTF composition has good rheological properties to facilitate manufacturing of sensors by conventional printing processes.

Through a unique combination of platinum group metal electrocatalysts and graphite materials, a low cost electrocatalyst system containing as low as 0.5/99.5 of metal/graphite ratio produces a biosensor working electrode to detect glucose levels of 100 nano-molar. This unique electrocatalyst in combination with a thermoplastic resin solution provides a low cost and reliable graphite-based PTF conductive composition for use in making disposable biosensors.

In this invention, the PTF conductive composition comprises the following components: (A) metal electrocatalyst selected from the platinum group which converts a chemical signal to an electrical signal (B) a conductive filler particles that provide electrical conductive pathways for the electrical signal, (C) a polymer that serves as the matrix resin holding (A) and (B) in a coating adhering to a plastic film substrate, and (D) an organic vehicle when mixed with the other ingredients make a composition for easy processing and printing of sensors.

A. Electrocatalyst

Electrocatalysts may be utilized in the present invention in two forms: (1) platinum group metal powders or (2) platinum group metals deposited on electrically conductive supports.

(1) Platinum group metal powders

Precious metals are well known for their catalytic activity for organic and inorganic reactions as well as catalytic electrochemical reactions. The metals for use in the invention are metals from the platinum group which are platinum, palladium, rhodium, iridium, ruthenium, osmium and mixtures thereof. Platinum is particularly preferred for use as a electrocatalyst in working electrodes.

For use in a PTF composition, the metal particles are finely divided powder form. Furthermore, a metal powder with high surface area and very small particle size is preferred. Such a metal powder not only reduces metal cost but also provides superior catalytic activity. Metal powder catalysts, such as platinum black, typically has a surface area of >5 $m^2/g$ and is suitable for the metal-graphite compositions covered in this invention. Metal powder catalysts with very high surface area (>65 $m^2/g$) lead to high sensor background current. Fuel cell grade platinum black powders having a typical surface area of 25–60 $m^2/g$, commercially available from Colonial Metals Inc., Elkton, Md. and Alfa Aesar, Ward Hill, Mass., are particularly suitable. Precious metal powders with surface areas of <5 $m^2/g$, commonly used in thick film compositions for electronics applications, do not have sufficient catalytic activity for sensor applications. Therefore, surface areas >5 $m^2/g$ are preferred.

(2) Platinum group metals deposited on electrically conductive supports(metallized graphite)

Metallized graphite is platinum group precious metal particles and mixtures thereof directly attached to support particles. Supported metals offer potential benefits of high electrocatalytic activity through direct electron-transfer from catalytic sites to the conductive network. The most widely used and preferred catalyst support for use as electrocatalysts is graphite, which is commonly used in carbon electrodes. Graphite offers not only good electrical conductivity but also low electrochemical signal interference because of its inertness to electrochemical reaction. Metallized graphite suitable for use as the electrocatalyst has about 0.5–10% metal based weight on graphite. Higher metal loading not only make sensors unacceptably costly for disposable sensor applications but also leads to background current noise due to high activity in catalyzed side reactions. To achieve high catalytic activity and low material cost, it is also desirable that catalyst particles be deposited in microcrystalline size, typically <10 nm. Metallized graphite can be prepared using a method described in the U.S. Pat. No. 4,044,193. Metallized graphite can be modified to form a modified metallized graphite which enriches the surface functional groups on the graphite which interact with metal catalyst particles. Surface modification processes effective for graphite materials are reduction with strong reducing agents and plasma etching processes. Strong reducing agents such as sodium hypophosphite, sodium borohydride, sodium bisulfite and sodium formate are effective in producing modified metallized graphite materials that show improved sensor performance.

The amount of metal in finely divided metal powder and/or in metallized graphite (referred to collectively as "metal") in the composition based on solids is about 0.1–5% wt. with a preferred range of 0.3–3% wt. and more preferred of 1–2.5% wt. The preferred metal/graphite ratio is in the range of 5/95 to 0.5/99.5.

B. Graphite Conductive Filler

Graphite is commonly used as the conductive filler forming the conductive network in the carbon composition electrodes. Graphite materials suitable for sensor working electrodes may be synthetic; pyrolytic, or natural graphite. Synthetic graphite made from petroleum coke that have good balance of low metal impurities (usually <500 ppm metal contamination) and rich surface functional groups are preferred. Pyrolytic graphite made from natural gas (such as UCP-2 graphite from Carbone of America, Bay City, Mich.) and purified graphites which are purified by a high temperature electro-crystallization process (such as 8315 graphite from Asbury Graphite, Asbury, N.J.) tend to have less surface functional groups for interacting with metal catalysts. Generally, platinum carbon electrodes with pyrolytic or purified graphites tend to have poor sensor performance. Also, natural graphite tends to have poor purity which may lead to high background current noise and potential risk of catalyst poisoning.

Therefore, preferred graphite materials typically have particles with diameters of about 1–30 microns with mean particle diameter in the range of 2–10 micron. Larger graphite particles tend to cause problems in screen printing. Finer graphite particles which have high surface areas tend to raise the background current. Graphite materials can also be modified by the same method as the modified metallized graphite described above.

If metal powder is used in the composition then the amount of graphite and/or modified graphite powder added to the composition based on solids is in the range of 62–85% by weight. When using metallized graphite powder, the graphite supports used in the metallized graphite particles are found in the composition in a range of 62–85% by weight based on solids in the composition. Additional graphite and/or modified graphite may be added to the composition to adjust the weight % of the platinum group metals. In order to achieve good electrical conductivity the volume ratio of graphite/binder is maintained in the range of 75/25 to 45/55.

C. Polymer Binder

Thermoplastics are preferred polymeric binders in the composition. Unlike PTF compositions with thermoset binders which require long curing time at high temperature, thermoplastic based PTF compositions can be used in a quick printing-drying process suitable for reel-to-reel sensor fabrication. Suitable thermoplastic binders provide a matrix that holds the electrocatalyst and graphite particles together and forms a coating with good scratch resistance and good adhesion to plastic film substrates. Thermoplastic resins for use in the invention have a glass transition temperature >40C and are selected from the group of acrylic, polyester, vinyl resins, polyimide, and polycarbonate polymers. It is important that the thermoplastic polymers contains no electrochemically active impurities which contribute to background current noise. Polymers which contain aromatic groups on the polymer chain or side chains are preferred. Examples are styrene-containing acrylic copolymers poly (styrene-acrylonitrile) (such as Tyril resins from Dow Chemicals, Midland, Mich.), benzyl methacrylate acrylic copolymer, poly(butadiene-acrylonitrile-styrene), poly (styrene), poly(hydroxyether) (such as UCAR phenoxy resins from Phenoxy Specialties, Rock Hill, S.C.), copolyester resins with tera-, iso- or phthalate aromatic groups (such as Vitel resins from Goodrich, Arkon, Ohio.), polycarbonate (such as Lexan resin from General Electric, Pittsfield, Mass.) and polyimide (such as Ultem resins from General Electric). The aromatic groups on the polymers enhance the wetting of the polymers on graphite surfaces, and thus reduce printing defects such as pinholes caused by polymer de-wetting during printing and drying. The polymeric binders can be dissolved in solvents, or solvent blends to provide a vehicle for making metal-graphite compositions suitable for screen printing.

In the dry electrode coating, the amount of binder is in the range of 14–35% by weight. A lower binder level results in a porous coating which has low scratch resistance and high background current. A higher binder level leads to low electrical conductivity and low electrocatalytic activity, and thus unacceptable sensor performance.

D. Surfactant

The precious metal powder is further dispersed to form a colloidal dispersion by milling the powder in a polymer solution, and a surfactant is added to help stabilize the dispersion catalyst particles. It is not necessary to use a surfactant if modified graphite is used in the composition; therefore, they may be used in combination or separately. Surfactant molecules tend to migrate to the air surface during drying of the print and thus provide a way to modify the hydrophobicity of Pt/C electrode surface. A surfactant with hydrophilic end groups, such as ethylene oxide units, can improve the wetting of the electrode by water and also enhances sensor performance.

Surfactant is found in the present invention at 0.01–3% wt. based on solids. Surfactants suitable for the platinum black dispersion are from the group of long-chain fatty acid or their sodium salt, nonionic surfactants such as long-chain fatty alcohol, non-ionic surfactants based on poly(ethylene oxide)-modified fatty acid, fatty alcohol and alkylphenol (such as surfactants under the trade names of Triton®, Tergitol® from Union Carbide, CT).

E. Solvent

A solvent suitable for the composition should meet the following criteria: a) be able to dissolve the polymer binder; b) have low electrochemical activity and minimal electrochemically active impurities so that very low background current can be achieved; c) have a moderate evaporation rate which quickens drying during sensors printing and production; d) be inert to Pt-catalyzed chemical reactions, such as auto-ignition which can cause safety problem during manufacturing and processing. Most hydroxyl-containing organic solvents, such as alcohol or glycol alkyl ether do not meet requirements (b) and (d), and are not suitable for the PTF composition. Solvents, such as dibasic esters which contain electrochemically active alcohol impurities also are not suitable. Solvents from the groups of alkyl and aryl ketones, aromatic hydrocarbon, glycol diacetates and glycol acetates or mixtures thereof were found to be suitable solvents producing compositions with low sensor background current. Aromatic hydrocarbon solvents which tends to have good wetting on graphite surfaces provides an additional benefit in imparting a slightly shear thinning rheology on the composition and thus improves the printing of graphite based electrodes.

A typical metal-graphite composition may be prepared as follows: (1) a binder solution is prepared by dissolving a thermoplastic polymer in a suitable solvent; (2) a dispersion of metal powder in the binder solution is then prepared by roll-milling; (3) a mixture of binder solution, metal powder dispersion, graphite and/or metallized graphite and solvent are mixed by high speed dispersion methods to make the PTF composition. The resultant composition typically has a viscosity in the range of 10–100 Pa.S and a % solids of 25–40% suitable for screen printing.

F. Sensor Fabrication and Testing Criteria

The electrochemical sensor used for testing sensor performance of the composition of the present invention is based on a three-electrode design containing a working electrode, a counter electrode and a reference electrode. The working electrode is about a 1 $cm^2$ disk of the metal-graphite composition with 10–30 um thickness. Both the counter electrode and the reference electrode are prints of a silver/silver chloride PTF composition as found in recently allowed U.S. Ser. No. 08/921,183. The sensor is printed on a 5 mil polyester film substrate using a conventional screen printing process. Typically, the printing is done in a multiple print-dry sequence which lays down conductive patterns of electrical contacts for measuring equipment attachments. Dielectric coatings are applied for protecting conductive lines. Sensor testing was done using a custommade potentiostat.

Three key tests were performed: (TEST A) electrochemical sensor response to hydrogen peroxide and (TEST B) biosensor response to glucose and (TEST C) effect of temperature on biosensor. TEST A is done in a specially designed test cell which holds a 10 mil thick layer of test solution on top of the three-electrodes of the sensor. The cell is filled with a phosphate buffered saline solution (PBS) having pH of 7.5, 0.1 M phosphate and 77 mM NaCl, and the background current is recorded as the steady-state current measured between the working electrode and the counter electrode after a current bias with the potential of the working electrode set against the reference electrode at 0.75 V for 10 minutes and at 0.4 V for 50 minutes. Then the current response of the sensor after a $H_2O_2$ solution is injected in the test cell is recorded vs time. A series of current measurements are made with different $H_2O_2$ concentrations. The slope of a linear plot of the current measured at a fixed time point, such as at 60 seconds, against the $H_2O_2$ concentration provides a measure of the sensor sensitivity to $H_2O_2$. An sensor sensitivity of 20–70 $nA/cm^2$.uM of $H_2O_2$ with background current noise in the range of 2–20 nA is acceptable. The preferred range is a sensor sensitivity of >50 $nA/cm^2$.uM of $H_2O_2$ with a background current noise of <5 nA.

TEST B is done on a biosensor which has an enzyme-containing gel disk placed on top of the three electrodes of an electrochemical sensor. The gel disk contains a poly (ethylene oxide) gel, NaCl and phosphate buffer, and glucose oxidase enzyme for glucose oxidation and hydrogen peroxide generation. The biosensor is pre-conditioned with the working electrode on a 0.77 V bias for 10 minutes followed by a 0.42 V bias for 50 minutes, and the steady-state current measured at the end is the background current. Then 10 micro-liter volume of a 0.2 mM glucose solution sample is added to the gel. The current response is recorded verses time. The charge/electron response at time (t) from the glucose sample can be calculated by integrating over time (t) the current response minus the background current. The charge response at time (t) divided by the theoretical total charge generated from the glucose sample gives the % charge response (% recovery) recovered by the biosensor at time 2.5 minute provides a measure of the sensitivity of the biosensor to glucose. Glucose recovery >20% at 2.5 minute recovery time were acceptable results, but more preferred is >30% at 2.5 minute recovery time.

TEST C is done on a biosensor that has an enzyme-containing gel disk placed on top of the three electrodes of an electrochemical sensor, as in TEST B. The biosensor is first held at 32° C., and the working electrode is preconditioned for 10 minutes at 0.77 V bias followed by 50 minutes at 0.42 V bias. The background current is then measured every fifteen minutes over the next 7 hours. During each 15 minute cycle, the 0.42 V bias is first turned off for 5 minutes and then turned on for 10 minutes. The background current is measured and recorded over the 10 minute duration. The last background current reading provides the baseline background current for each 10 minute cycle. The transient background current is calculated by subtracting the baseline background current from the measured background current. Integration of the transient background current over the 10 minute period provides the total background signal due to the biosensor. After 3 hours of measurements at 32° C., the temperature is raised to 37° C., and after the temperature is stabilized the transient background current at 37° C. is measured and the total background signal calculated. A total background signal at 32° C. of <35,000 nano-Coulomb (nC) is acceptable. An increase in background signal of <15%/° C. is acceptable.

The present invention will be described in further detail by giving practical examples. The scope of the present invention, however, is not limited in any way by these practical examples.

EXAMPLES

The following formulations were used in Examples 1–6:

Polymer solution (A) was prepared by dissolving 25 parts of poly(styrene-acrylonitrile) in 75 parts of ethylene glycol diacetate.

Platinum dispersion (B) was prepared by milling on a 3-roll mill of a mixture containing 42 parts of Polymer solution (A), 24.67 parts of ethylene glycol diacetate and 33.33 parts of platinum black (Colonial Metals Inc., Elkton Md.).

Modified graphite sample (C) was prepared by treating 600 grams of synthetic graphite (Timrex SFG-15 from Timcal America, Ohio.) with 3600 grams of a 3% aqueous solution of sodium hypophosphite monohydrate at 65° C. for 90 minutes and then washed and dried at 120° C.

EXAMPLE 1

This examples demonstrate the preparation of PTF composition with a Pt/graphite ratio of 1/99 using platinum powder and a modified graphite as the electrocatalyst. A platinum-graphite composition was prepared by mixing 22.8 parts of Polymer solution (A), 49.6 parts of ethylene glycol diacetate, 24.8 parts of modified graphite and 0.8 part of Platinum dispersion (B). Printed sensor was tested as above. TEST A resulted in a typical sensor sensitivity of 48–51 nA/uM $H_2O_2$ and background current of 9–10 nA and TEST B in a glucose % recovery of 40–50%. The net paste composition was as follows:

| Ingredient | Weight Percent |
| --- | --- |
| Poly(styrene-acrylonitrile) | 6.05 |
| Ethylene glycol diacetate | 68.38 |
| Platinum black | 0.27 |
| Modified graphite (C) | 25.3 |

EXAMPLE 2

A platinum-graphite composition having a Pt/graphite ratio of 2.5/97.5 was prepared by mixing 11.2 parts of Polymer solution (A), 24.5 parts of ethylene glycol diacetate, 12.6 parts of modified graphite and 1.0 parts of Platinum dispersion (B). Printed sensor was tested as above. TEST A resulted in a sensor sensitivity of 67–70 nA/uM $H_2O_2$, a background current of 8–12 nA and TEST B in a glucose % recovery of 50–60%. The net paste composition was as follows:

| Ingredient | Weight Percent |
| --- | --- |
| Poly(styrene-acrylonitrile) | 6.1 |
| Ethylene glycol diacetate | 67.62 |
| Modified graphite (C) | 25.6 |
| Platinum black | 0.68 |

EXAMPLE 3

A Pt/C paste having modified graphite, surfactant and 0.37% Pt in dry weight was prepared in the same way as Example 1. A platinum black dispersion with 6% Triton*X 100 surfactant to Platinum dispersion B was prepared in the same way as Platinum dispersion (B). The Pt/C paste was prepared by mixing 21.4 parts of Polymer solution A, 14.0 parts of Aromatic 150, 28.0 parts of butyl cellosolve acetate, 24.8 parts of modified graphite, 0.40 parts of platinum black dispersion, and 0.40 parts of Triton*X 100. Printed sensor was tested as above. TEST A resulted in a sensor sensitivity of 41–48 nA/uM $H_2O_2$, a background current of 19 nA, and TEST B in glucose recovery of 35–37%. The net paste composition was as follows:

| Ingredient | Weight Percent |
| --- | --- |
| Poly(styrene-acrylonitrile) | 6.3 |
| Modified graphite (C) | 28.0 |
| Platinum black | 0.15 |
| Triton* X100 (1) | 0.03 |
| Ethylene glycol diacetate | 18.12 |
| Aromatic 150 | 15.8 |
| Butoxyethyl acetate (1) | 31.6 |

(1) Union Carbide, Danbury, CT

EXAMPLE 4

A platinum-graphite composition having a nonionic surfactant added to enhance sensor performance was prepared in the same way as Example 4 by mixing 10.7 grams of Polymer solution (A), 14.8 grams of 2-butoxyethyl acetate, 7.3 grams of Aromatic 150, 12.4 grams of graphite, 0.20 grams of Triton® X45 and Pt dispersion (B). Printed sensor was tested as above. TEST A resulted a sensitivity of 40 nA/uM of $H_2O_2$, a background current of 4 nA, and TEST B in a glucose % recovery of 44%. The net paste composition was as follows:

| Ingredient | Weight Percent |
|---|---|
| Poly(styrene-acrylonitrile) | 6.15% |
| Ethylene glycol diacetate | 18.3% |
| 2-Butoxyethyl acetate | 32.0% |
| Aromatic 150 | 15.6% |
| Triton ® X45 (2) | 0.43% |
| Synthetic graphite | 26.8% |
| Platinum black | 0.72% |

(2) Triton ® X45, Union Carbide, Danbury, CT

EXAMPLE 5

A Pt/C having a metal powder and platinized graphite as the electro-catalyst was prepared by mixing 21.4 parts of Polymer solution A, 50.0 parts of ethylene glycol diacetate, 19.6 parts of synthetic graphite, 0.018 parts of Trtiton*X45 surfactant, 3.1 parts of Platinum dispersion B, and 5.2 parts of platinized graphite. Printed sensor was tested as above. TEST A resulted in a sensor sensitivity of 41–51 nA/uM $H_2O_2$, a background current of 3 nA, and TEST B in a glucose recovery of 33–37%. TEST C resulted in a total background signal of 30,200 nC at 32° C., and 51,000 nC at 37° C. The net paste composition was as follows:

| Ingredient | Weight Percent |
|---|---|
| Poly(styrene-acrylonitrile) | 5.6 |
| Ethylene glycol diacetate | 68.38 |
| Synthetic graphite | 19.74 |
| Platinized graphite | 5.23 |
| Platinum black | 1.04 |
| Triton*X45 | 0.01 |

EXAMPLE 6 (COMPARATIVE)

A platinum-graphite composition containing a high purity graphite was prepared in a similar same way as Example 1 by mixing 21.4 grams of Polymer solution (A), 10.7 grams of ethylene glycol diacetate, 6.3 grams of Aromatic 150, 24.8 grams of purified graphite, 0.20 grams of Triton surfactant, 4.00 grams of platinum dispersion (B). Working electrodes printed with this composition were found to be full of pin-holes and the sensors had a sensitivity of 15 nA/uM of $H_2O_2$, a background current of 4.5 nA and a glucose % recovery of 3.3%.

| Ingredient | Weight Percent |
|---|---|
| Poly(styrene-acrylonitrile) | 8.9% |
| Ethylene glycol diacetate | 26.7% |
| Purified graphite (11) | 36.8% |
| Aromatic 150 | 9.3% |
| Platinum black | 2.0% |
| 2-butoxyethyl acetate | 15.8% |
| Triton ® X45 | 0.5% |

(11) Asbury A625, Asbury Mills Inc. Asbury, NJ

What is claimed is:

1. A conductor composition for use in electrochemical sensor applications, comprising, based on solids:

(a) 0.1–5% wt. conductive metal particles selected from the group consisting of finely divided powders of platinum group metals and mixtures thereof, (b) 62–85% wt. of modified graphite; and (c) 14–35% wt. of a thermoplastic polymer.

2. The conductor composition of claim 1 further comprising surfactant.

3. The composition of claim 2 wherein the surfactant is a nonionic surfactant selected from the group consisting of fatty acid, fatty alcohol, long-chain alkylphenol, poly (ethylene oxide)-modified fatty acid, fatty alcohol and alkylphenol.

4. The composition of claim 1 or 2 further comprising organic solvent.

5. The composition of claim 1 wherein the thermoplastic binder is selected from the group consisting of poly (styrene), styrene-containing acrylic copolymer, poly (acrylonitrile-butadiene-styrene), poly(hydroxyether), copolyester, poly(carbonate), and polyimide.

6. The composition of claim 1 or 3 wherein the organic solvent is selected from the group consisting of glycol ether acetate, glycol diacetate, alkyl ketone, aryl ketone, aromatic hydrocarbon and mixtures thereof.

7. A working electrode for use in electrochemical biosensor comprising the conductor composition of claim 1 or 2 on a substrate.

* * * * *

UNITED STATES PATENT AND TRADEMARK OFFICE
CERTIFICATE OF CORRECTION

PATENT NO. : 6,042,751
DATED : March 28, 2000
INVENTOR(S) : Man-Sheung Chan and Donald W. Kuty It is certified that error appears in the above-identified patent and that said Letters Patent is hereby corrected as shown below:

Column 10, line 44, delete "1 or 3" and substitue --4-- therefor.

Signed and Sealed this

Twenty-fourth Day of April, 2001

Attest:

NICHOLAS P. GODICI

Attesting Officer

Acting Director of the United States Patent and Trademark Office